(12) United States Patent
Chueh et al.

(10) Patent No.: US 7,631,540 B2
(45) Date of Patent: Dec. 15, 2009

(54) GAS SENSOR WITH NANOWIRES OF ZINC OXIDE OR INDIUM/ZINC MIXED OXIDES AND METHOD OF DETECTING NOX GAS

(75) Inventors: Miao-Ju Chueh, Hsinchu (TW); Pi-Guey Su, Hsinchu (TW); Yih-Shiaw Huang, Hsinchu (TW); I-Cherng Chen, Hsinchu (TW); Tung-Sheng Shih, Hsinchu (TW)

(73) Assignee: Industrial Technology Research Institute, Chutung Hsinchu (TW)

( * ) Notice: Subject to any disclaimer, the term of this patent is extended or adjusted under 35 U.S.C. 154(b) by 3 days.

(21) Appl. No.: 11/898,677

(22) Filed: Sep. 14, 2007

(65) Prior Publication Data
US 2008/0006078 A1 Jan. 10, 2008

Related U.S. Application Data

(62) Division of application No. 11/126,242, filed on May 11, 2005.

(51) Int. Cl.
*G01N 27/12* (2006.01)
(52) U.S. Cl. .................................................... 73/31.06

(58) Field of Classification Search ........................ None
See application file for complete search history.

(56) References Cited

U.S. PATENT DOCUMENTS

| 7,141,859 | B2 * | 11/2006 | DeBoer et al. ............... 257/414 |
| 2003/0139003 | A1 * | 7/2003 | Gole et al. ................... 438/200 |
| 2004/0161949 | A1 * | 8/2004 | Yadav et al. ................. 438/800 |
| 2005/0009224 | A1 * | 1/2005 | Yang et al. ..................... 438/57 |
| 2005/0072213 | A1 * | 4/2005 | Besnard et al. ............. 73/31.06 |
| 2005/0133476 | A1 * | 6/2005 | Islam et al. ..................... 216/2 |
| 2006/0091022 | A1 * | 5/2006 | Ruud et al. .................. 205/775 |
| 2006/0134392 | A1 * | 6/2006 | Hantschel et al. ........... 428/210 |

OTHER PUBLICATIONS

Paul Horowitz and Winfield Hill, The Art of Electronics, 2nd ed., 1995, pp. 4-9.*

* cited by examiner

*Primary Examiner*—Daniel S Larkin
(74) *Attorney, Agent, or Firm*—Bacon & Thomas, PLLC

(57) ABSTRACT

A gas sensor is disclosed, which includes two separate metal electrodes on a surface of a substrate and a semiconductor thin film deposited on the surface of the substrate and connecting the two metal electrodes. The semiconductor thin film contains zinc oxide or a mixed oxide of zinc and indium, and the zinc oxide or the mixed oxide of zinc and indium are in the form of nanowires which constitute a gas-sensing surface of the semiconductor thin film. The nanowires have a diameter of 50-900 nm. The present invention also discloses a method for detecting the presence of a NOx gas.

8 Claims, 5 Drawing Sheets

US 7,631,540 B2

GAS SENSOR WITH NANOWIRES OF ZINC OXIDE OR INDIUM/ZINC MIXED OXIDES AND METHOD OF DETECTING NOX GAS

This application is a divisional application of pending U.S. application Ser. No. 11/126,242 filed May 11, 2005 (of which the entire disclosure of the pending, prior application is hereby incorporated by reference).

FIELD OF THE INVENTION

The present invention relates to a semiconductor metal oxide type gas sensor, and particularly to a semiconductor metal oxide type gas sensor for detecting NOx gas, which comprises nanowires formed of zinc oxide or a mixed oxide of zinc and indium.

BACKGROUND OF THE INVENTION

Many toxic gases (e.g. CO, NOx, $H_2S$, and $CH_4$, etc.) are harmful to human body. These toxic gases are colorless and odorless such that they cannot be detected of their presence by human senses of vision and smell. When the concentration of toxic gases exceeds a certain level in air, a person will develop symptoms, such as headache, dizziness, vomiting, or even shock and death. An alarm can be timely dispatched in the event of a toxic gas concentration exceeding the permissible level to a human body, if a gas analysis instrument or device is used to monitor the gas composition in an enclosed space or an environment with poor ventilation in real time, thereby preventing the occurrence of misfortune and disaster.

A gas sensor is a device for converting a detected gas concentration into an electric signal. Conventional gas sensors include: electrochemical gas sensors, and semiconductor metal oxide gas sensors, etc.

Although an electrochemical gas sensor can perform a detection of gas concentration at room temperature, the reference electrode thereof is liable to a chemical buildup which causes a drifting of the gas detection baseline and thus a need in recalibration and inconvenience in use.

A semiconductor metal oxide type gas sensor uses the variation of resistance caused by the amount of gas adsorbed on the surface of an oxide to monitor a variation of the gas concentration in the surrounding of the sensor. Such a gas sensor has the following advantages: good heat resistance and corrosion resistance, simple in production, easy in combination with microelectromechanical techniques, easy in transportation, low power consumption, and easy in application commercially, etc. The construction of such a gas sensor essentially includes a ceramic substrate, a detection material layer, a heater, and measurement electrodes, etc., wherein the detection material layer mainly consists of a polycrystalline and porous film of a metal oxide. For example, $SnO_2$, ZnO [U.S. Pat. No. 4,358,951], $Fe_2O_3$, $In_2O_3$, and $WO_3$, etc. are all suitable as a detection material layer for such a sensor. Major defects of such a sensor; however, include poor gas sensitivity, gas selectivity, and stability. Usually, in order to accelerate the desorption rate of a gas chemically adsorbed on the surface of an oxide detection material, a semiconductor metal oxide type sensor needs to be operating at a higher temperature, e.g. 300~450° C., so that the response time of the sensor can be enhanced. However, the oxide is liable to undergo an irreversible change in its electrical properties after operating at a high temperature environment over a long period of time, thereby causing a drifting in the measured signal. Meanwhile, a few problems, e.g. size of the sensor, high electric power consumption, and maintaining at a constant temperature, etc., are also derived from the requirement of heating. As a result, such type of gas sensor tends to have higher production and operation costs.

ZnO is an n-type multifunctional semiconductor material due to its high chemical stability, low dielectric constant, and high luminous transmittance, and is widely used in dielectric ceramics, catalysts, and detection materials. Regarding the detection function, ZnO is one of the materials found and widely used in the earlier days. However, ZnO has the defects of high operating temperature (>150° C.) and poor selectivity.

SUMMARY OF THE INVENTION

One major objective of the present invention is to provide a resistance type gas sensor having a quick reaction, a quick response and a wide linear detection range at room temperature.

Another objective of the present invention is to provide a novel and simple method for producing a resistance type gas sensor having a quick reaction, a quick response and a wide linear detection range at room temperature.

In order to achieve the above-mentioned objectives, the present invention uses a vapor-liquid-solid reaction mechanism to deposit nanowires of zinc oxide or nanowires of mixed oxide of zinc and indium on a substrate as a gas semiconductor film.

BRIEF DESCRIPTION OF THE DRAWINGS

FIG. 1b shows a schematic bottom plan view of the gas sensor shown in FIG. 1a.

FIG. 1c shows a schematic side view of the gas sensor shown in FIG. 1a.

Figure 1A:
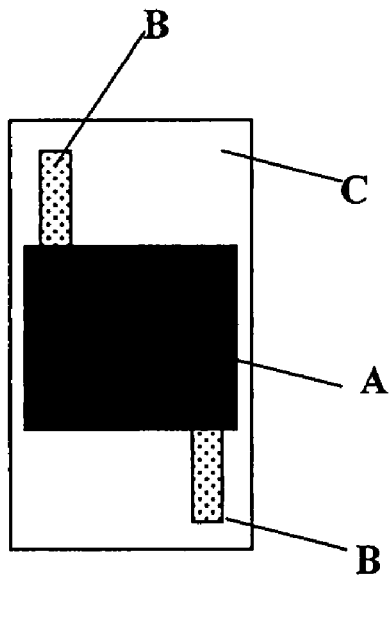
FIG. 1a shows a schematic top plan view of a gas sensor prepared according to Example 1 of the present invention.

| Legends: | |
|---|---|
| A ... semiconductor film; | C ... alumina single crystal substrate; |
| B, D ... gold electrode; | E ... $RuO_2$ |

DETAILED DESCRIPTION OF THE INVENTION

The present invention discloses a gas sensor, which comprises:

a substrate, preferably a ceramic substrate;

two separated metal electrodes located on a surface of said substrate;

a semiconductor film deposited on the surface of said substrate and connecting said two metal electrodes; which is characterized in that:

said semiconductor film comprises zinc oxide or a mixed oxide of zinc and indium, and said zinc oxide or said mixed oxide of zinc and indium are in the form of nanowires which constitute a gas-sensing surface of said semiconductor film, wherein said nanowires have a diameter of 5-900 nm.

Preferably, said semiconductor film is composed of the mixed oxide of zinc and indium.

Preferably, said semiconductor film is composed of zinc oxide.

Preferably, said two separated electrodes are parallel to each other and are made of gold, platinum, or an alloy thereof, and more preferably gold.

The present invention also discloses a method for detecting the existence of $NO_x$ in a gas sample, which comprises exposing said gas-sensing surface of the gas sensor of the present invention to said gas sample; measuring an electric signal resulting from a variation in electric resistance between the two electrodes of said gas sensor; and comparing said electric signal with a preset value, and determining whether $NO_x$ exists in said gas sample based on a difference between the electric signal and the preset value, wherein x=1~2.

Preferably, a reference resistance is connected in series with said gas sensor, and a constant voltage is applied on two ends of the resulting connection of said reference resistance and said gas sensor, and said electric signal is obtained by measuring a voltage drop across said reference resistance. More preferably, said preset value is a voltage drop of said reference resistance measured when the gas detection surface of said gas sensor is exposed to air.

Preferably, said gas detection surface is not heated by any energy other than an energy entrained by said gas sample and an energy generated by measuring said electric signal, when said gas detection surface of said gas sensor is exposed to said gas sample.

Preferably, said $NO_x$ gas is $NO_2$.

The present invention will be better understood through the following examples which are for illustration and not for limitation of the scope of the present invention.

EXAMPLE 1

An electrode of a semiconductor film was produced by performing a screen-printing process on the front face of an alumina single crystal substrate (96%, thick film grade) using a gold paste. After the screen-printing process, the electrode was dried with an IR drier, and then sintered at 850° C.

The resulting substrate was placed at location near a rear end in a quartz tube in a heating furnace. A zinc oxide powder (99.999%, 350 mesh, Strem Chemicals) and a metal zinc powder (99.999%, 350 mesh, Strem Chemicals) were mixed in a molar ratio of 1:1. The resulting mixture was loaded into an alumina crucible, then placed at an intermediate section in the quartz tube 20-35 mm away from the substrate. Argon gas was introduced at a rate of 35 sccm from the front end of the quartz tube into the quartz tube, and a mechanical pump was used to control the quartz tube to be at a pressure of about 100 Torr. The heating furnace was operating at 500-700° C. The reaction time was 30-60 minutes. Upon completion of the reaction and after the furnace had cooled down, the product was removed from the furnace and nanowires of zinc oxide were deposited on said substrate in a substantially perpendicular orientation.

In order to experimentally testing the performance of a gas sensor at different temperatures, prior to the deposition of nanowires of zinc oxide, a heater was formed on the back of said substrate by screen-printing a gold paste, drying the gold paste with an IR drier, followed by sintering at 850° C., the resulting gold film was to provide soldering leads. Next, a $RuO_2$ as a heater material was screen-printed therein and dried.

Figure 1B:
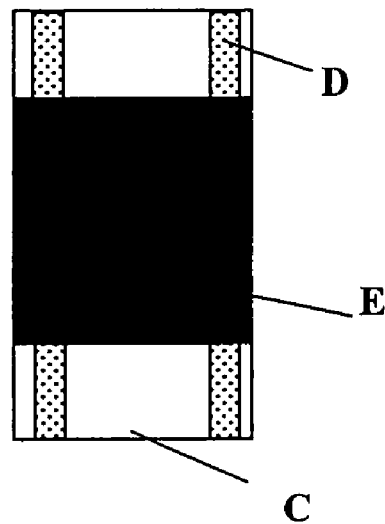
Figure 1C:
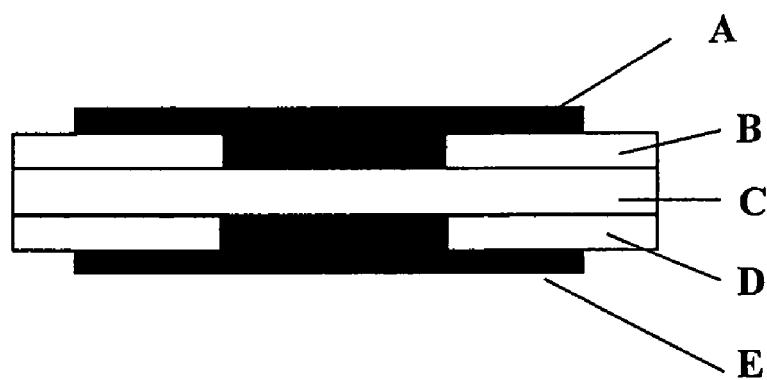
Figure 2:
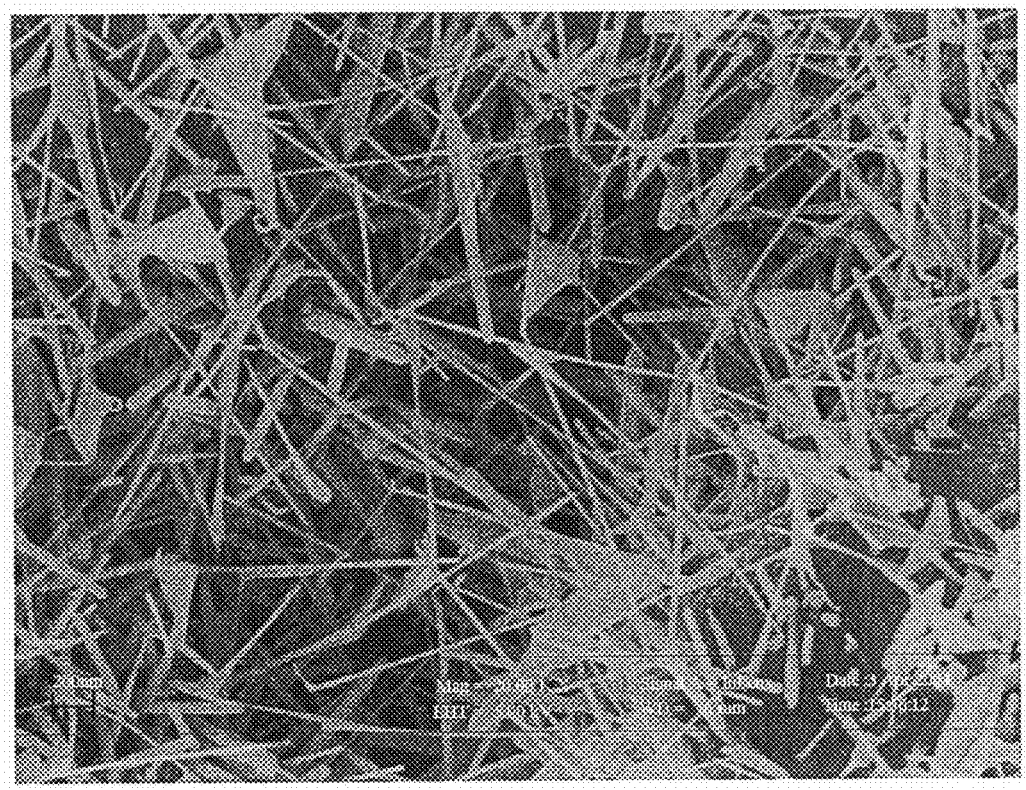
FIG. 2 shows a FESEM photo of nanowires of zinc oxide prepared according to Example 1 of the present invention.

FIGS. 1a to 1c show a gas sensor prepared according to this example, wherein the substrate was 4 mm in length and 2.5 mm in width; A represents a semiconductor film having nanowires of zinc oxide on the surface thereof; B and D represent a gold electrode; C represents an alumina single crystal substrate; and E represents $RuO_2$;

FIG. 2 shows a Field Emission Scanning Electron Microscope (FESEM) photo of a semiconductor film with nanowires of zinc oxide prepared according to this example, wherein a large proportion of the nanowires of zinc oxide have a diameter of 45-50 nm and a length larger than 400 nm.

EXAMPLE 2

In addition to a zinc oxide powder (99.999%, 350 mesh, Strem Chemicals) and a metal zinc powder (99.999%, 350 mesh, Strem Chemicals), a metal Indium powder (99.999%, 350 mesh, Strem Chemicals) was added, the procedures in Example 1 were repeated to prepare a gas sensor having a semiconductor film with nanowires of a mixed oxide of zinc and indium. The mixed oxide contained a zinc oxide powder, a metal zinc powder, and a metal indium in a weight ratio of 45:45:10.

Figure 3:
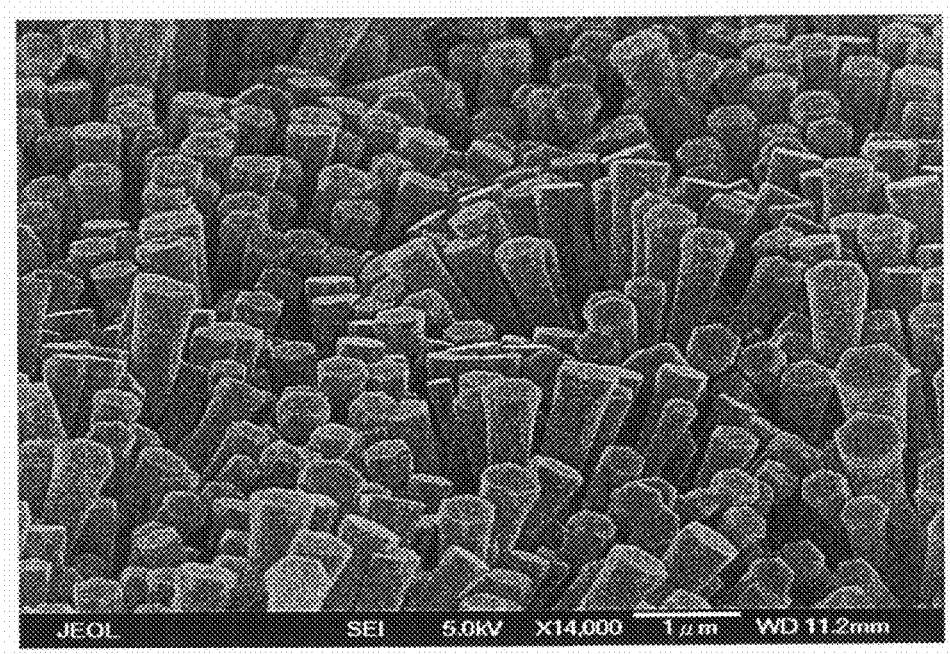
FIG. 3 shows a FESEM photo of nanowires of a mixed oxide of zinc and indium prepared according to Example 2 of the present invention.

FIG. 3 shows a FESEM photo of a semiconductor film with nanowires of a mixed oxide of zinc and indium prepared according to this example, wherein a large proportion of the nanowires of zinc oxide have a diameter of 200-800 nm and a length larger than 1 μm.

Tests:

A gas sensor from Example 1 or 2 was connected in series to a reference resistance. A constant voltage of 5.0 V was applied on the two ends of the resulting serial connection of the reference resistance (about 100 ohm at room temperature) and the gas sensor, and a voltage drop ($V_{out}$) of said reference resistance was measured.

Figure 4:
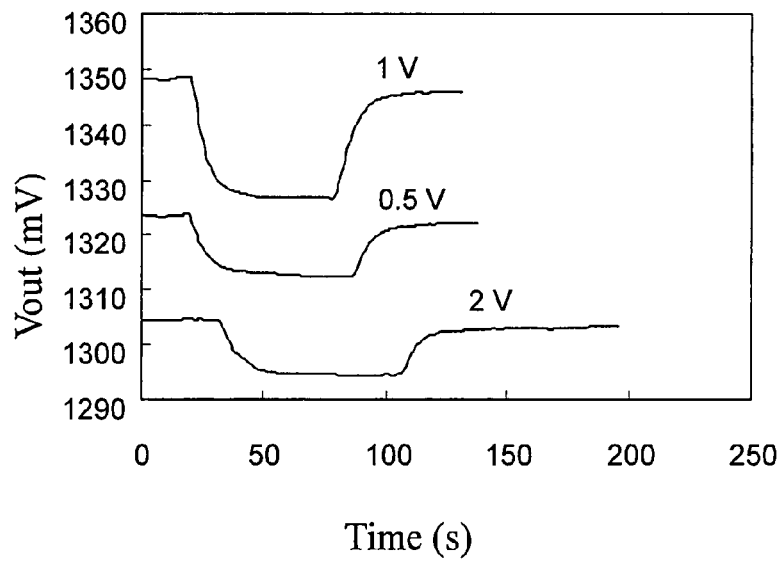
FIG. 4 shows the sensitivity of the gas sensor prepared according to Example 1 of the present invention, when the heater is applied with 0V, 0.5V, and 1.0V, respectively, wherein the ordinate is a voltage drop ($V_{out}$) of said reference resistance, and the abscissa is time.
Figure 5:
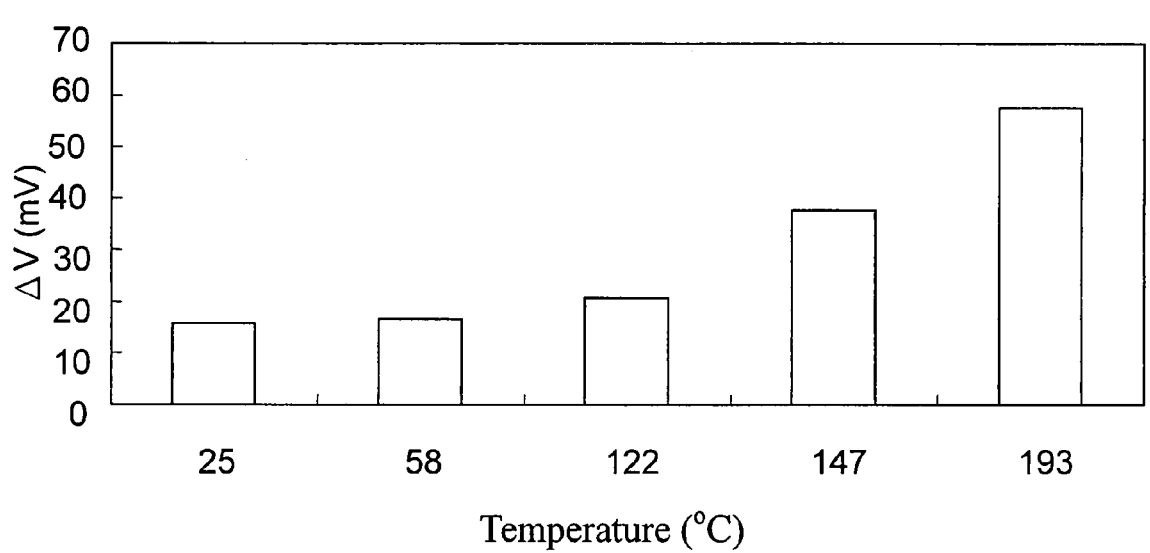
FIG. 5 shows the sensitivity of the gas sensor prepared according to Example 1 of the present invention at a normal temperature and various heating temperatures, wherein the ordinate is the difference ($\Delta V$) of voltage drops of the reference resistance measured for the gas mixture containing 100 ppm $NO_2$ and without $NO_2$, and the abscissa is temperature.

A mixture gas containing 100 ppm of $NO_2$ and the balance of air was passed through a gas sensor prepared in Example 1, and the measured results are shown in FIGS. 4 and 5. FIG. 4 shows the sensitivity of the gas sensor according to Example 1, when the heater thereof was applied with 0V, 0.5V, and 1.0V, respectively; wherein the ordinate is a voltage drop ($V_{out}$) of said reference resistance. FIG. 4 indicates that the voltage drop across said reference resistance drops rapidly to a constant value and maintains at said value when the gas mixture containing 100 ppm of $NO_2$ passes through the gas sensor according to the present invention; and the voltage drop recovers more than 90% when only air passes through the gas sensor. The magnitude of the voltage drop increases as an the voltage applied on the heater increases. FIG. 5 shows the sensitivity of the gas sensor according to Example 1 at room temperature and various heating temperatures, wherein the ordinate is the difference ($\Delta V$) of voltage drops of the reference resistance measured for the gas mixture containing 100 ppm $NO_2$ and without $NO_2$. FIG. 5 indicates that the gas sensor according to the present invention produced a signal with a differential value of 18 mV at room temperature, and the signal becomes more prominent along with an increase in temperature.

Figure 6A:
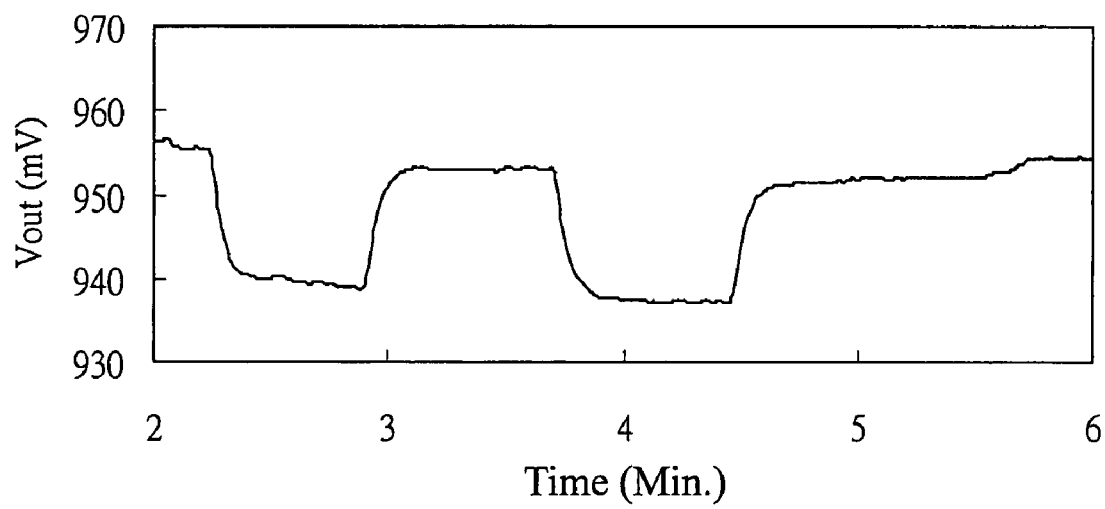
FIG. 6a shows the sensitivity of the gas sensor prepared according to Example 1 of the present invention, when the gas mixture containing 100 ppm of $NO_2$ is introduced intermittently twice, wherein the ordinate is a voltage drop ($V_{out}$) of said reference resistance, and the abscissa is time.
Figure 6B:
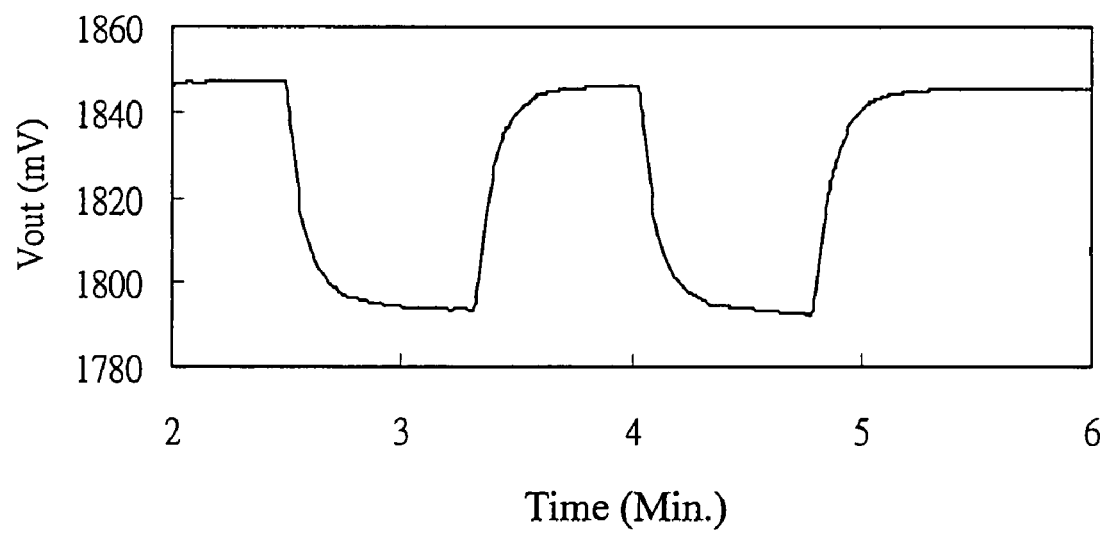
FIG. 6b shows the sensitivity of the gas sensor prepared according to Example 2 of the present invention, when the gas mixture containing 100 ppm of $NO_2$ is introduced intermittently twice, wherein the ordinate is a voltage drop ($V_{out}$) of said reference resistance, and the abscissa is time.

FIGS. 6a and 6b separately show the test results similar to FIG. 4 where no voltage was applied on the heater of the gas sensor. However, the gas mixture containing 100 ppm of $NO_2$ is introduced intermittently twice. FIG. 6a shows the results of the gas sensor prepared according to Example 1, and FIG. 6b shows the results of the gas sensor prepared according to Example 2.

Figure 7A:
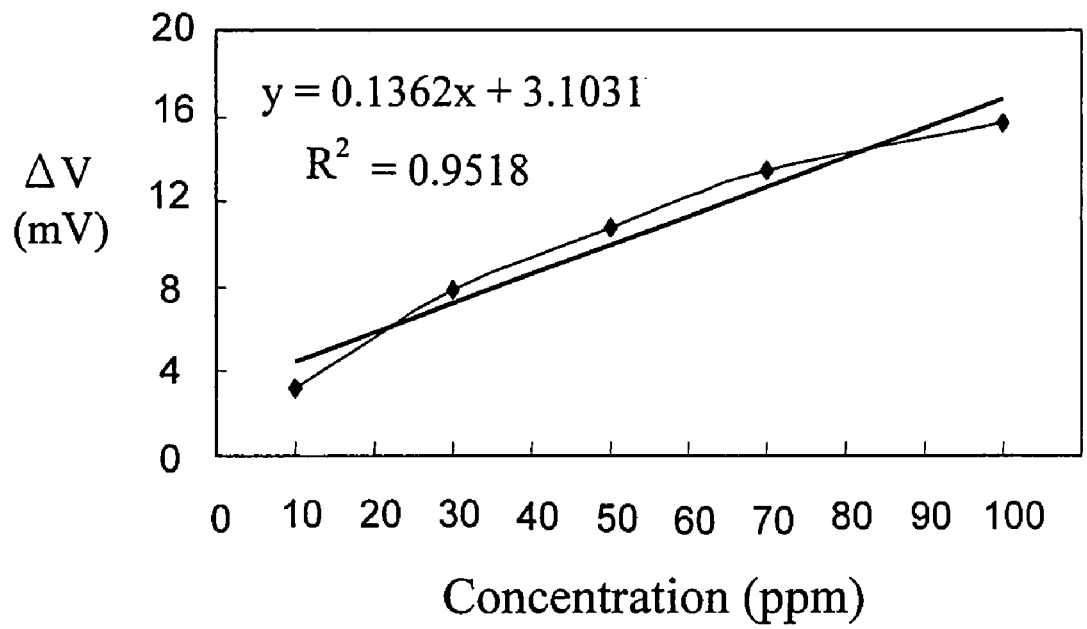
FIG. 7a shows differences ($\Delta V$) of voltage drops of said reference resistance, when the gas sensor prepared according to Example 1 of the present invention is exposed to gas mixtures containing, respectively, 10, 30, 50, 70, and 100 ppm of $NO_2$; wherein a linear equation representing the relationship between the difference (ΔV) (mV) of voltage drops of said reference resistance and the concentration of $NO_2$ is listed.
Figure 7B:
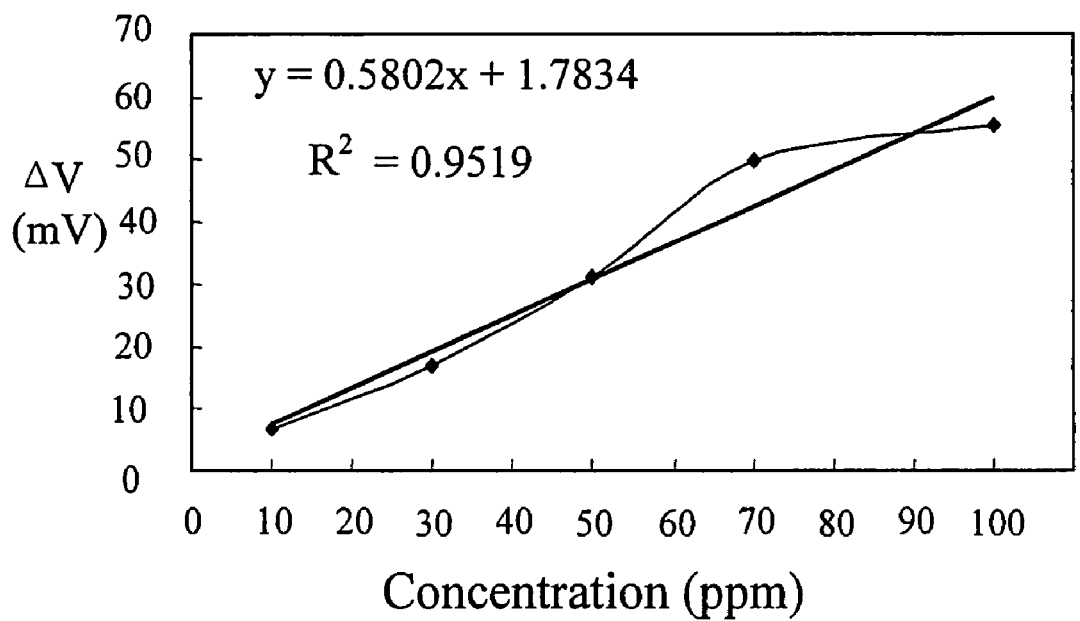
FIG. 7b shows differences (ΔV) of voltage drops of said reference resistance, when the gas sensor prepared according to Example 2 of the present invention is exposed to gas mixtures containing, respectively, 10, 30, 50, 70, and 100 ppm of $NO_2$; wherein a linear equation representing the relationship between the difference (ΔV) (mV) of voltage drops of said reference resistance and the concentration of $NO_2$ is listed.

FIGS. 7a and 7b separate show test results similar to FIG. 5 at room temperature. However, the gas mixtures containing, respectively, 10, 30, 50, 70 and 100 ppm of $NO_2$ are intermittently introduced. FIG. 7a shows the results of the gas sensor prepared according to Example 1, and FIG. 7b shows the results of the gas sensor prepared according to Example 2. A linear equation represents the relationship between the difference ($\Delta V$) of voltage drops of said reference resistance and the concentration of $NO_2$ is also listed in FIGS. 7a and 7b.

The results of FIG. 6a to FIG. 7b indicate that the addition of Indium increases the sensitivity of nanowires of zinc oxide for about three folds.

The invention claimed is:

1. A method for detecting the existence of $NO_x$ in a gas sample with a gas sensor, said gas sensor comprising:
    a substrate;
    two separated metal electrodes located on a surface of said substrate;
    a semiconductor film deposited on the surface of said substrate and connecting said two metal electrodes; wherein
    said semiconductor film comprises zinc oxide or a mixed oxide of zinc and indium, and said zinc oxide or said mixed oxide of zinc and indium are in the form of nanowires which constitute a gas-sensing surface of said semiconductor film, wherein said nanowires have a diameter of 5-900 nm and in a substantially perpendicular orientation to the surface of the substrate,
    said method comprising exposing said gas-sensing surface of the gas sensor to said gas sample; measuring an electric signal resulting from a variation in electric resistance between the two electrodes of said gas sensor; and comparing said electric signal with a preset value, and determining whether $NO_x$ exists in said gas sample based on a difference between the electric signal and the preset value, wherein x=1~2.

2. The method as claimed in claim 1, wherein said gas detection surface is not heated by any energy other than an energy entrained by said gas sample and an energy generated by measuring said electric signal, when said gas detection surface of said gas sensor is exposed to said gas sample.

3. The method as claimed in claim 1, wherein said $NO_x$ gas is $NO_2$.

4. The method as claimed in claim 1, wherein said semiconductor film is composed of the mixed oxide of zinc indium.

5. The method as claimed in claim 1, wherein said semiconductor film is composed of zinc oxide.

6. The method as claimed in claim 1, wherein said substrate is a ceramic substrate.

7. The method as claimed in claim 1, wherein said two separated electrodes are parallel to each other and are made of gold, platinum, or an alloy thereof.

8. The method as claimed in claim 7, wherein said two separated electrodes are made of gold.

* * * * *